(12) United States Patent
Levin

(10) Patent No.: US 6,629,950 B1
(45) Date of Patent: *Oct. 7, 2003

(54) FLUID DELIVERY SYSTEM

(76) Inventor: John M. Levin, 412 Fairview Rd., Narberth, PA (US) 19072

( * ) Notice: Subject to any disclaimer, the term of this patent is extended or adjusted under 35 U.S.C. 154(b) by 0 days.

This patent is subject to a terminal disclaimer.

(21) Appl. No.: 09/244,621

(22) Filed: Feb. 3, 1999

Related U.S. Application Data

(60) Provisional application No. 60/073,635, filed on Feb. 4, 1998.

(51) Int. Cl.⁷ ............................................. A61M 11/00
(52) U.S. Cl. .................................................. 604/93.01
(58) Field of Search ........................... 604/890.1, 891.1, 604/131, 132, 93, 8; 128/899, DIG. 12; 600/16

(56) References Cited

U.S. PATENT DOCUMENTS

| | | | | |
|---|---|---|---|---|
| 3,641,591 A | * | 2/1972 | Kolff | 600/16 |
| 3,732,865 A | * | 5/1973 | Higuchi et al. | 604/892.1 |
| 3,910,283 A | | 10/1975 | Leveen | 128/350 |
| 4,240,434 A | | 12/1980 | Newkirk | 128/350 |
| 4,630,597 A | * | 12/1986 | Kantrowitz et al. | 600/18 |
| 4,668,231 A | * | 5/1987 | de Vries et al. | 604/891.1 |
| 4,718,894 A | * | 1/1988 | Lazorthes | 604/288.02 |
| 4,931,050 A | * | 6/1990 | Idriss | 604/891.1 |
| 5,271,746 A | | 12/1993 | Pol et al. | 623/3 |
| 5,273,518 A | * | 12/1993 | Lee et al. | 600/16 |
| 5,318,501 A | | 6/1994 | Lee et al. | 600/16 |
| 5,397,349 A | * | 3/1995 | Kolff et al. | 600/16 |
| 5,738,627 A | * | 4/1998 | Kovacs et al. | 600/16 |
| 5,746,762 A | * | 5/1998 | Bass | 604/96 |
| 5,813,410 A | | 9/1998 | Levin | 128/897 |
| 5,868,142 A | * | 2/1999 | Dahlborn | 128/899 |

* cited by examiner

Primary Examiner—Brian L. Casler
Assistant Examiner—Kevin C. Sirmons
(74) Attorney, Agent, or Firm—Caesar, Rivise, Bernstein, Cohen & Pokotilow, Ltd.

(57) ABSTRACT

A fluid delivery system that is implantable in the body for delivering treatment fluids to a person. The delivery system includes a fluid-containing sack positioned in the body which is responsive to internal pressure changes resulting from the breathing pattern of the person. The delivery system also includes a fluid delivery conduit which communicates with the sack through a one-way valve. The conduit is provided for directing treatment fluid out of the delivery system in response to the breathing pattern of a patient and delivering the treatment fluid to a desired region of the person's body in repetitive dosages over a sustained period of time.

15 Claims, 1 Drawing Sheet

FLUID DELIVERY SYSTEM

RELATED APPLICATIONS

This is a utility application based upon Provisional Patent Application Ser. No. 60/073,635, filed Feb. 4, 1998, entitled Fluid Delivery System. Applicant hereby incorporates the entire subject matter of the '635 provisional application into this utility application and also claims the benefit of the filing date of the '635 provisional application for this utility application.

BACKGROUND OF THE INVENTION

Internal body pumps are known. The applicant herein has invented one such internal body pump which employs the breathing patterns of an individual to operate. That body pump is the subject of U.S. Pat. No. 5,813,410 and is entitled Internal Body Pump And Systems Employing The Same. To applicant's knowledge there has never been a delivery system that is controlled by the breathing patterns of a person and that is arranged for delivering continuous, repetitive doses of a treatment fluid to a desired region of the person's body over a sustained period of time. This invention is intended to be used to deliver a wide variety of treatment fluids, such as chemotherapy fluids, hormones, insulin and fluids to treat hypoparathyroidism (i.e., calcium and magnesium).

OBJECTS OF THE INVENTION

Accordingly, it is a general object of this invention to provide a fluid delivery system which overcomes the disadvantages of the prior art.

It is a further object of this invention to provide a fluid delivery system which is inexpensive to manufacture.

It is a further object of this invention to provide a fluid delivery system that is reliable in operation.

It is a further object of this invention to provide a fluid delivery system that is simple in construction.

It is a further object of this invention to provide a fluid delivery system that is controlled by the breathing patterns of a person and that is arranged for delivering continuous, repetitive doses of a treatment fluid to a desired region of the person's body over a sustained period of time.

SUMMARY OF THE INVENTION

These and other objects of this invention are achieved by providing a fluid delivery system. The fluid delivery system is implantable in the body of a person and is provided for delivering treatment fluids to the person. The delivery system includes a fluid-containing sack positioned in the body which is responsive to internal pressure changes resulting from the breathing pattern of the person. The delivery system also includes a fluid delivery conduit which communicates with the sack through a one-way valve. The conduit is provided for directing treatment fluid out of the delivery system in response to the breathing pattern of a patient and delivering the treatment.fluid to a desired region of the person's body in repetitive dosages over a sustained period of time.

DESCRIPTION OF THE DRAWINGS

Other objects and many attendant features of this invention will become readily appreciated as the same becomes better understood by reference to the following detailed description when considered in connection with the accompanying drawing wherein.

DETAILED DESCRIPTION OF THE PREFERRED EMBODIMENTS

Figure 1:
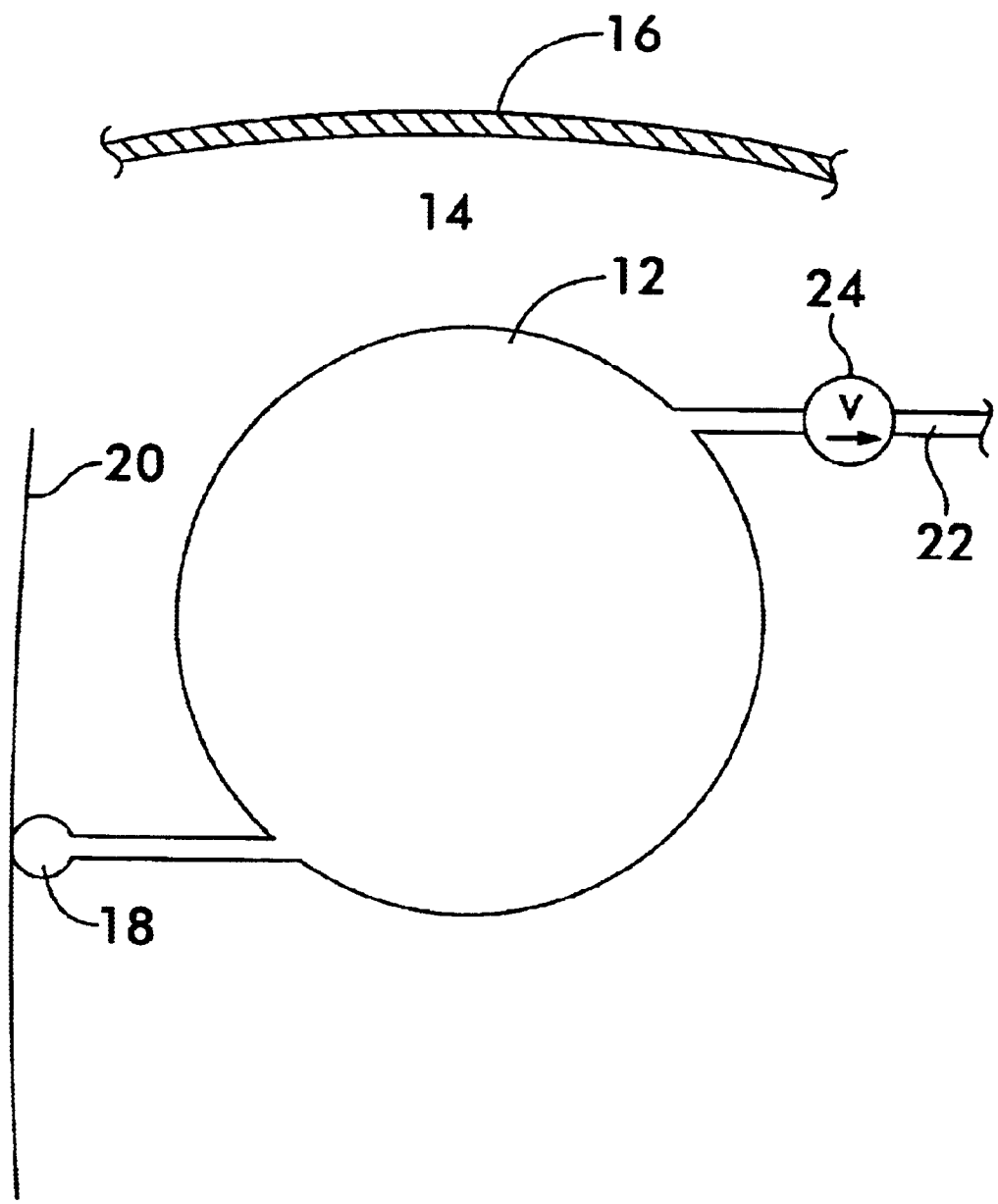
FIG. 1 is an elevational view of a unique internal body pump of this invention, showing its preferred location relative to the diaphragm within the body.

Referring now in greater detail to the sole drawing, FIG. 1, wherein like reference numerals refer to like parts, the unique delivery system of this invention includes a fluid retaining sack 12, which in the preferred embodiment is formed of an inelastic but flexible plastic material compatible with the body. The sack 12 initially is completely flat, but is illustrated in its expanded condition with the fluid to be dispensed in it. Most preferably, the sack 12 is located in the abdominal region 14 of the patient below diaphragm 16; although placement of the sack in the thoracic region of the patient above the diaphragm also is within the scope of this invention.

To assist in filling the sack 12 with a desired fluid to be dispensed within the body, a subcutaneous access reservoir 18 is provided in communication with the sack and is positioned closely adjacent the person's skin (schematically illustrated at 20) so that the sack can be filled percutaneously with a small syringe containing the desired fluid. Most preferably the plastic material of the reservoir 18 has the ability to reseal itself after the needle of the syringe has been removed.

A delivery conduit 22 communicates with the sack 12 through a one-way valve 24. The normal breathing pattern of a patient causes the change in internal body pressure to act upon the sack 12 to force the treatment fluid out of the sack, and through the one-way valve 24 and the delivery conduit 22.

The internal body region that communicates with the delivery conduit 22, and means for directing treatment fluid, depends upon the type of treatment fluid being administered over a sustained period of time.

For example, for some applications, such as in administering systemic chemotherapy fluid, the delivery conduit 22 communicates directly with the systemic venous system. To administer regional chemotherapy, such as to the liver, the delivery conduit 22 can communicate with the portal venous system. When delivering insulin the delivery conduit 22 can communicate with the intraparatoneal cavity, or can be located directly in the subcutaneous tissue.

As mentioned earlier, fluid flow from the sack 12 through delivery conduit 22 is created by taking advantage of the normal breathing function of a person, and in particular, the effect that the normal breathing function has on movement of the person's diaphragm 16. Specifically, during inspiration (inhaling) the diaphragm 16, which separates the thoracic and abdominal cavities, is forced to descend; thereby leading to an increase in the intrathoracic volume and a corresponding decrease in the intrathoracic pressure. Conversely, the volume of the abdominal cavity 14 decreases and the pressure in that cavity increases. This action forces fluid from the sack 12 located within the abdominal cavity through delivery conduit 22 and into a desired region of a person's body, in desired, repetitive dosages over a sustained period of time. It should be noted that the flow from the sack 12 into the body is limited to one direction, in view of the placement of the one-way valve 24 within the delivery conduit 22.

In accordance with the exemplary embodiment of the present invention, the unique delivery system includes holding means for storing treatment fluid in a patient. The holding means includes the sack 12. The exemplary delivery system also includes transfer means communicating with the holding means and directing the treatment fluid out of the delivery system in response to the breathing pattern of the patient and delivering the treatment fluid to a desired region of the patient's body in repetitive dosages over 2 sustained period of time. The transfer means includes the delivery conduit 22. Moreover, the exemplary delivery system includes control means for communicating the treatment fluid from the holding means to the transfer means and for inhibiting communication of the treatment fluid from the transfer means to the holding means. The control means includes the one-way valve 24.

It should be appreciated that various modifications to the present invention may be made to the embodiment described above without departing from the spirit and scope of the invention as defined in the appended claims.

I claim:

1. A fluid delivery system adapted to be implanted in a body of a patient for delivering treatment fluid to the patient, said delivery system including a fluid-containing sack positioned in the body, said fluid-containing sack is responsive to internal pressure changes resulting from the breathing pattern of the patient, a fluid delivery conduit having a proximal end communicating with the sack and a distal end adapted to communicate with a desired region of the body, said delivery conduit adapted to direct the treatment fluid out of the delivery system into the desired region in response to the breathing pattern of the patient and in repetitive dosages over a sustained period of time, and a one-way valve, said fluid delivery conduit communicating with said sack through said one-way valve.

2. The delivery system of claim 1 wherein the distal end of the delivery conduit is adapted to connect directly to the systemic venous system of the person.

3. The delivery system of claim 1 wherein the distal end of the delivery conduit is adapted to connect directly connected to the portal venous system.

4. The delivery system of claim 1 wherein the delivery conduit directs treatment fluid into either the abdominal cavity or into subcutaneous tissue of the patient.

5. The delivery system of claim 1, further including a subcutaneous reservoir located adjacent a person's skin through which fluids to be delivered to the body are directed into the sack.

6. The delivery system of claim 1, wherein said fluid-containing sack is formed substantially of an elastic material.

7. The delivery of system claim 6, wherein said fluid-containing sack includes a first side and a second side opposite the first side, said first and second sides formed substantially of the elastic material.

8. The delivery system of claim 1, wherein a plurality of breathing cycles are required for delivery of the repetitive dosages of the treatment fluid to the desired region.

9. A fluid delivery system adapted to be implanted in a body of a patient for delivering treatment fluid to the patient, said delivery system comprising:

a fluid-containing sack positioned in the body, said fluid-containing sack responsive to internal pressure changes resulting from the breathing pattern of the patient;

a fluid delivery conduit communicating with the fluid-containing sack, said delivery conduit adapted to direct treatment fluid out of the delivery system in response to the breathing pattern of the patient, said delivery conduit adapted to deliver the treatment fluid to a desired region of the patient's body in repetitive dosages over a sustained period of time; and a one-way valve, said fluid delivery conduit communicating with said fluid-containing sack through said one-way valve.

10. The delivery system of claim 9, wherein the delivery conduit is adapted to connect directly to the systemic venous system of the patient.

11. The delivery system of claim 9, wherein the delivery conduit is adapted to connect directly to the portal venous system of the patient.

12. The delivery system of claim 9, further comprising a subcutaneous reservoir located adjacent the patient's skin, said subcutaneous reservoir communicating with said fluid-containing sack to deliver the treatment fluid to said sack.

13. The delivery system of claim 9, wherein said delivery conduit includes a coupling end communicating with the sack and a free end that delivers the treatment fluid out of the fluid delivery system to the desired region.

14. A fluid delivery system implantable in a patient for delivering treatment fluids to the patient, said delivery system comprising:

holding means for storing the treatment fluid in the patient, said holding means positioned in the patient for responding to internal pressure changes resulting from the breathing pattern of the patient;

transfer means communicating with said holding means, said transfer means directing the treatment fluid out of the delivery system in response to the breathing pattern of the patient and delivering the treatment fluid to a desired region of the patient's body in repetitive dosages over a sustained period of time; and control means for communicating the treatment fluids from said holding means to said transfer means, said control means inhibiting communication of the treatment fluid from the transfer means to the holding means.

15. The delivery system of claim 14, further comprising means for directing the treatment fluid into one of an abdominal cavity or a subcutaneous tissue of the patient.

* * * * *